United States Patent [19]

Iwagiri et al.

[11] 4,337,246

[45] Jun. 29, 1982

[54] SOLID PREPARATION COMPRISING COBAMAMIDE OR MECOBALAMIN

[75] Inventors: Susumu Iwagiri, Gifu; Teiichi Hattori, Inuyama; Teruyoshi Nasu, Tsushima; Yasuo Miyake, Inuyama, all of Japan

[73] Assignee: Eisai Co., Ltd., Tokyo, Japan

[21] Appl. No.: 200,122

[22] Filed: Oct. 24, 1980

[30] Foreign Application Priority Data

Nov. 22, 1979 [JP] Japan ................................ 54-150743

[51] Int. Cl.$^3$ ...................... A61K 31/00; A61K 47/00
[52] U.S. Cl. .................................................... 424/174
[58] Field of Search ........................................ 424/174

[56] References Cited

U.S. PATENT DOCUMENTS 2,959,520  11/1960  Kawagiri ........................ 424/174 X

FOREIGN PATENT DOCUMENTS 45-35798  of 1970  Japan .
46-29740  of 1971  Japan .

OTHER PUBLICATIONS

Merck Index, 9th Ed., (1976) Entry No. 2404.

*Primary Examiner*—Stanley J. Friedman
*Attorney, Agent, or Firm*—Blanchard, Flynn, Thiel, Boutell & Tanis

[57] ABSTRACT

A solid preparation according to the invention comprises cobamamide or mecobalamin as an effective ingredient and a red dye suitable for food as a stabilizer to light.

10 Claims, 5 Drawing Figures

SOLID PREPARATION COMPRISING COBAMAMIDE OR MECOBALAMIN

This invention relates to a solid preparation comprising cobamamide or mecobalamin which is made stable to light, especially to a solid preparation comprising cobamamide or mecabalamin, being stable to light, in which the cobamamide or mecobalamin is present together with a red coloring matter. A preferred embodiment of the invention is the solid preparation in which cobamamide or mecobalamin and the red coloring matter are present separately in different granules. As the coloring matter, New Coccine is most preferable.

Cobamamide and mecobalamin are both forms of coenzyme $B_{12}$. More particularly, cobamamide is a coenzyme $B_{12}$ included in the liver, and mecobalamin is a coenzyme $B_{12}$ included in the blood. Both can be used as therapeutic agents for treating pernicious anemia. Mecobalamin is further effective as a therapeutic agent for treating peripheral nerve disease.

It is known that a coenzyme $B_{12}$ is extremely unstable to light. Accordingly, a variety of arts have been proposed for stabilizing coenzyme $B_{12}$. Examples are as follows.

The following stabilizers have been added to an aqueous coenzyme $B_{12}$ solution: gelatin or dextran (Japanese Patent Publication (referred to, hereinafter, as JPP) No. 46(1971)-15320); a water-soluble coal tar dye (JPP No. 45(1970)-35798); a porphyrin compound, p-aminobenzoic acid or nicotinic amide (JPP No. 45(1970)-11920); fumaric acid (JPP No. 45(1970)-38552); dextran-iron, sodium glutamate or sodium citrate (Japanese Provisional Patent Publication No. 49(1974)-418); ascorbic acid or erythorbic acid (JPP No. 53(1978)-1810), or ethylene glycol or sorbitol (JPP No. 46(1971)-28093).

The coenzyme $B_{12}$ has been previously administered through injection in most cases. Accordingly, the prior arts cited above relate to stabilization of the aqueous solution of coenzyme $B_{12}$.

Recently, however, oral administration of the coenzyme $B_{12}$ has been increasingly adopted. Thus, the stabilization of the coenzyme $B_{12}$ in solid preparations has now been under study. In view of the fact that the cobamamide and mecobalamin incorporated into solid preparations are particularly unstable to light, the present inventors made studies for the purpose of providing a stabilizing means appropriate for the stabilization. As a result of the studies, it was found that the cobamamide or mecobalamin contained in a solid preparation shows high stability to light when it is present with red food dye in the preparation. The present invention has been completed based on this finding.

Japanese Patent Publication No. 45(1970)-35798 describes that the coenzyme $B_{12}$-containing injection solution can be stabilized against light by the addition of a water-soluble coal tar dye. In the examples 1 to 6 according to this publication, for instance, there are disclosed the additions of Evans' Blue, Methylene Blue, Indigo Carmine, phenolphthalein, methylrosaniline and Amaranth.

Japanese Patent Publication No. 46(1971)-29740 describes that aqueous methylcobalamin solution can be stabilized against light by the addition of a compound specifically absorbing light in the range of 250–600 m$\mu$. In the examples 1–10 of this publication, for instance, there are disclosed the additions of Amaranth (Red Dye No. 2) and Sunset Yellow (Yellow Dye No. 5).

Although the above-cited publications teach that a variety of compounds, such as a water-soluble coal tar and a light-absorbing compound, are useful as stabilizing agents for the coenzyme $B_{12}$ contained in an aqueous solution, the studies carried out by the present inventors uncovered that, particularly as to cobamamide and mecobalamin in a solid preparation, only the addition of a red food dye is effective for imparting stability to light to cobamamide and mecobalamin. Particularly excellent stabilizing effect can be given by New Coccine (Red Dye No. 102), according to the present studies.

As far as the solid preparation according to the invention is concerned, the cobamamide or mecobalamin and the red dye can be individually formed in respective granules in advance of the admixing, and then both types of granules are admixed to be present together. According to the studies, this individual granulating method can give the cobamamide or mecobalamin stability at the same level as or higher than the case in which the cobamamide or mecabalamin and the red dye are admixed in powder form, or in which both are admixed into a single granule.

The constitution of the invention for the stabilization in a solid preparation which is described above is therefore believed to be unobvious from the prior arts disclosing the stabilization of an aqueous coenzyme $B_{12}$.

Examples of the red dyes to be used in the present invention include Amaranth (Red Dye No. 2), Erythrocin (Red Dye No. 3), New Coccine (Red Dye No. 102), Phloxine (Red Dye No. 104), Rose Bengal (Red Dye No. 105) and Acid Red (Red Dye No. 106). Particularly, New Coccine provides an excellent appearance to the solid preparation, as well as effective stabilization, as shown hereinafter in the examples.

There is no specific limitation on the amount of the red dye to be added. The range in which 0.1 to 5 parts of the red dye are added against 1 part of the cobamamide or mecobalamin is preferred. This range can be applied when the cobamaimide or mecobalamin and the red dye are directly admixed in their powdery forms, or when they are admixed after the granulation steps.

When the cobamamide or mecobalamin and the red dye are individually granulated prior to the admixing, the ratio between both granules can vary optionally with the desired amount of the cobamamide or mecobalamin. If the mecobalamin content, for instance, should be 0.1%, granules containing 1% of mecobalamin are prepared initially and then the granules are diluted ten times with the separately prepared granules containing the red dye. That is to say, the respective granules are admixed in the ratio of 1:9.

Examples of granules of the present invention include the granules prepared by the cylindrical granulating method, as well as others such as fine granules prepared by the fluidized-bed granulating method. Accordingly, the granules to be employed for the individual granulating process wherein the cobamamide or mecobalamin and the red food dye are to be granulated separately can be optionally prepared by any of the conventional methods such as the cylindrical granulating method, the tumbling granulating method, the fluidized-bed granulating method, etc.

Representative examples of the solid preparations of the present invention include a powder, granules, a capsule and a tablet. Therefore, the cobamamide or mecobalamin and the red dye can be present together in the solid preparation under, in the first place, one of four states such as (1) a state in which both are present in a powdery preparation; (2) a state in which both are together present in the same granule; (3) a state in which one is present in granular form while the other is in a powdery form; and (4) a state in which both are present in the individually granulated form. Furthermore, these powders and granules can be encapsulated or tableted.

A pharmaceutical composition according to the invention, as shown above, comprises cobamamide or mecobalamin, a red dye suitable for food and a carrier. As the carrier, there may be used any conventional ones, for example, corn starch, lactose, mannitol, crystalline cellulose and hydroxypropyl cellulose.

The effect given by the present invention is shown below by the following examples.

[EXAMPLE OF EFFECT 1]

Specimen

Granules were prepared in the same manner as the procedure described in Example 1 (given hereinafter). Four kinds of specimens in which the New Coccine contents were 0.1%, 0.2%, 0.4% and 0.6%, respectively, were prepared. In the specimens, mecobalamin and New Coccine were together present in the same granule. A control specimen was prepared in the same manner as above, except that no New Coccine was included therein.

Test Method

In a Petri dish (diameter: 9 cm) was placed 4 g. of the specimen evenly so that the height of the specimen layer reached 1–2 mm. The so spread specimen was left under a fluorescent lamp at 1,000 Lux. Percentages of remaining mecobalamin was determined at regular intervals.

Results

Figure 1:
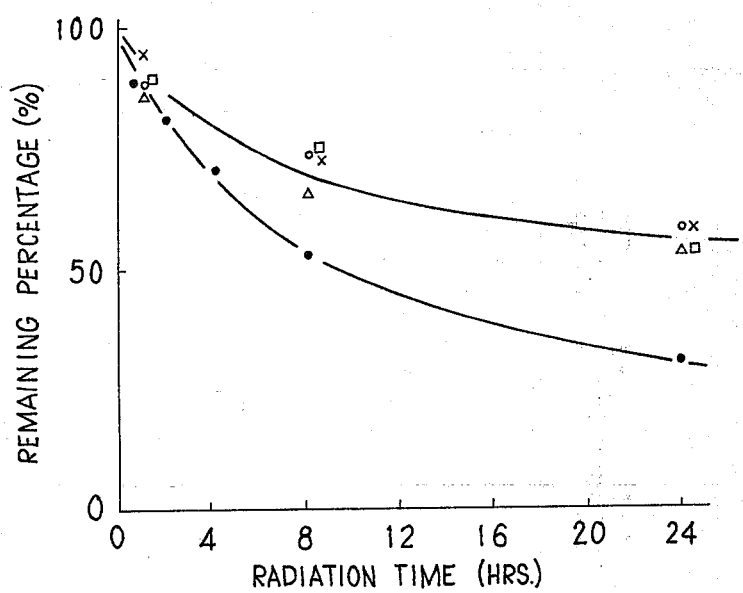
FIG. 1 shows the change of the percentage of remaining mecobalamin with the passage of time under conditions in which the mecobalamin and New Coccine were included in the same granule and 1,000 Lux of light was radiated onto the granules. In the figure, the lines indicate the cases in which the New Coccine contents were 0% (o), 0.1% (o), 0.2% (△), 0.4% (□) and 0.6% (x), respectively.

The results are illustrated in FIG. 1. It is evident according to FIG. 1 that New Coccine is effective in stabilizing mecobalamin against light.

[EXAMPLE OF EFFECT 2]

Specimen

Granules were prepared in the same manner as the procedure described in Example 2 (given hereinafter). Three kinds of specimens were prepared in which the New Coccine contents were 0.1%, 0.2% and 0.4%, respectively. In each specimen, mecobalamin and New Coccine had been individually granulated prior to the admixing. A control specimen employed was the same as that employed in Example of Effect 1.

Test Method

The same method as described in Example of Effect 1 was used.

Results

Figure 2:
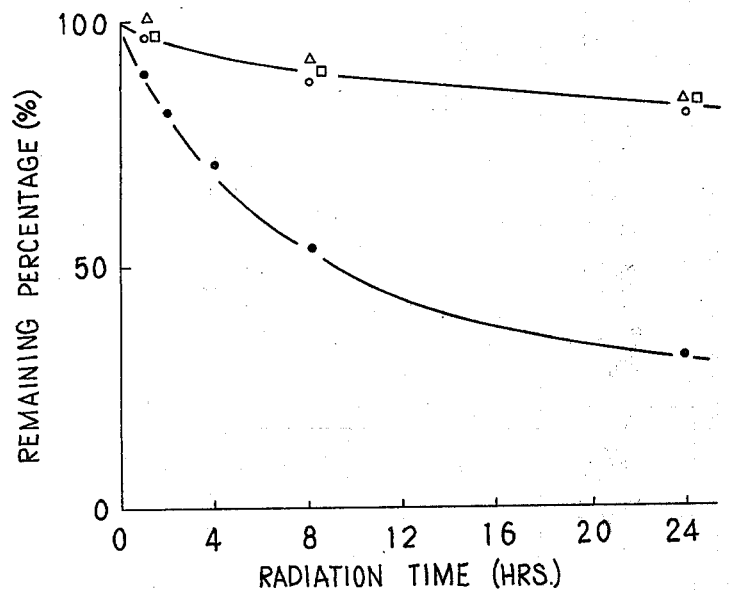
FIG. 2 shows the change of the remaining mecobalamin percentage with the passage of time under conditions in which the mecobalamin and New Coccine were included in different granules and 1,000 Lux of light was radiated onto the granules. In the figure, the lines indicate the cases in which the New Coccine contents were 0.1% (o), 0.2% (△), and 0.4 (□), respectively. The case employing the control specimen is indicated by the line marked (o).

The results are illustrated in FIG. 2. It is evident according to FIG. 2 that New Coccine gives higher light-stability to mecobalamin when New Coccine and mecobalamin are individually granulated in advance of the admixing into the preparation.

[EXAMPLE OF EFFECT 3]

Specimen

Granules were prepared in the same manner as in the procedure described in Example 3 (given hereinafter); the New Coccine content was adjusted to 0.2%. In the specimen, cobamamide and New Coccine had been individually granulated prior to the admixing. A control specimen was prepared in the same manner as described in Example 5 (given hereinafter) except that no New Coccine was included therein.

Test Method

The same method as described in Example of Effect 1 was used.

Results

Figure 3:
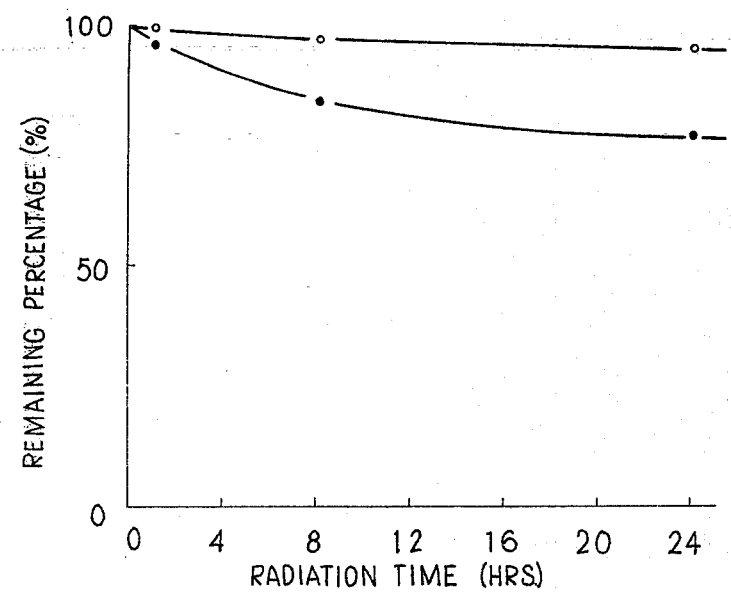
FIG. 3 shows the change of remaining cobamamide percentage with the passage of time under conditions in which the cobamamide and New Coccine were included in different granules and 1,000 Lux of light was radiated onto the granules. In the figure, the lines indicate the case in which the New Coccine content was 0.2% (o) and the control specimen (o), respectively.

The results are illustrated in FIG. 3. It is evident according to FIG. 3 that New Coccine gives higher light-stability to cobamamide when New Coccine and cobamamide are individually granulated in advance of the admixing into the preparation.

[EXAMPLE OF EFFECT 4]

Specimen

Capsules were prepared in the same manner as in the procedure described in Example 4 (given hereinafter); two kinds of specimens were prepared in which the New Coccine contents per one capsule were 0 mg. and 0.1 mg, respectively.

Test Method

The specimens were placed in a Petri dishes and kept under two conditions, that is, 8 hrs. times one month under 1,000 Lux (240,000 Lux.hrs) and 8 hrs. times three months under 1,000 Lux (720,000 Lux hrs). Then, percentages of the remaining portions were determined.

Results

The redults are set forth in the following table. According to the results, it is evident that New Coccine works well in the capsule preparation for imparting the stabilization to mecobalamin.

| New Coccine Content per one capsule | 240,000 Lux.hrs | 720,000 Lux.hrs |
|---|---|---|
| 0 mg. | 86.3% | 83.8% |
| 0.1 mg. | 95.7% | 95.0% |

[EXAMPLE OF EFFECT 5]

Specimen

Granules were prepared in the same manner as the procedure described in Example 1 (given hereinafter); four kinds of speciments were preferred, containing as the dye New Coccine (Red Dye No. 102), Erythrocin (Red Dye No. 3), Tartrazine (Yellow Dye No. 4) and Indigo Carmine (Blue Dye No. 2), respectively.

Test Method

The same method as described in Example of Effect 1 was used.

Results

Figure 4:
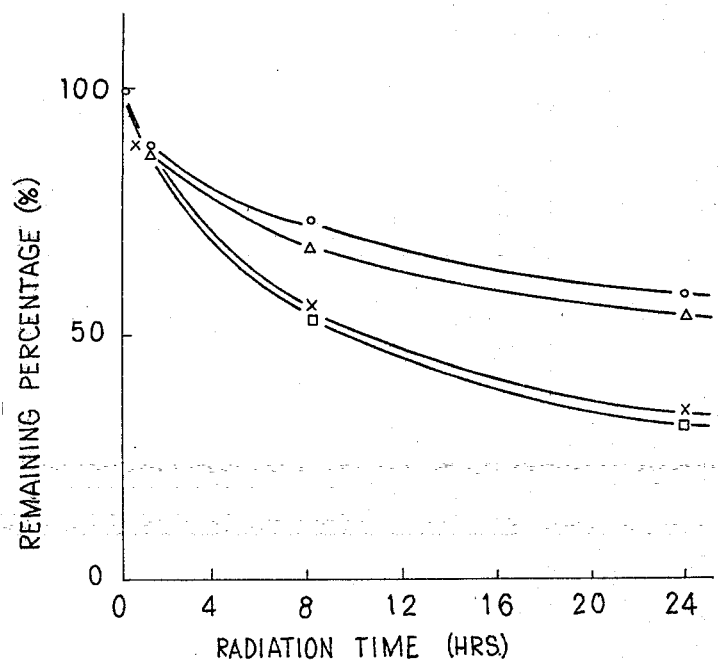
FIG. 4 shows the change of remaining mecobalamin percentage with the passage of time under the condition in which the mecobalamin and one of several food dyes were included in the same granule and 1,000 Lux of light was radiated onto the granules. In the figure, the lines indicate the cases in which the food dyes were New Coccine (o), Erythrocin (△), Tartrazine (x) and Indigo Carmine (□).

The results are illustrated in FIG. 4. According to FIG. 4, it is evident that the red dyes are specifically effective in giving the light-stabilization to mecobalamin.

[EXAMPLE OF EFFECT 6]

Specimen

Granules were prepared in the same manner as the procedure described in Example 5 (given hereinafter); five kinds of specimens were prepared, each containing as the dye New Coccine (Red Dye No. 102), Rose Bengal (Red Dye No. 105), Sunset Yellow (Yellow Dye No. 5), Fast Green (Green Dye No. 3) or Brilliant Blue (Blue Dye No. 1).

Test Method

The same method as described in Example of Effect 1 was used.

Results

Figure 5:
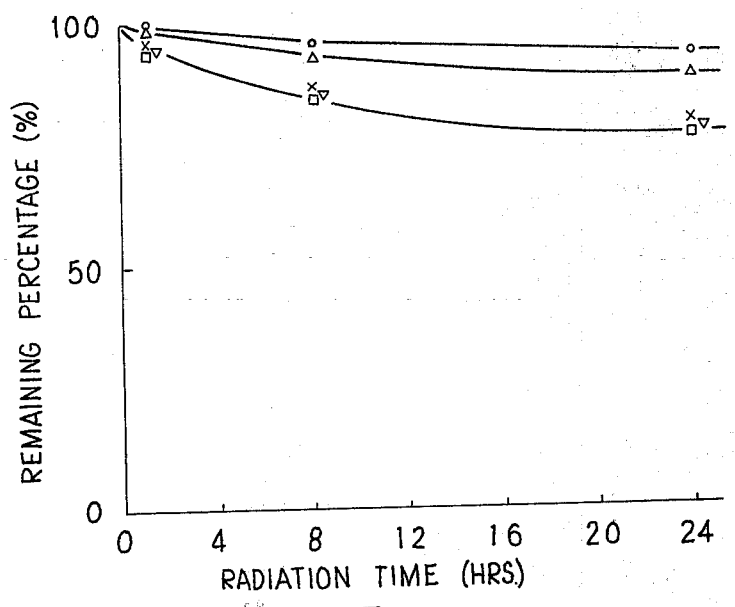
FIG. 5 shows the change of remaining cobamamide percentages with the passage of time under the condition in which the cobamamide and one of several food dyes were included in the same granule and 1,000 Lux of light was radiated onto the granules. In the figure, the lines indicate the cases in which the food dyes were New Coccine (o), Rose Bengal (△), Sunset Yellow (x), Fast Green (□), and Brilliant Blue (▽).

The results are illustrated in FIG. 5. According to FIG. 5, it is evident that the red dyes are specifically effective in giving the light-stabilization to cobamamide.

Preparations according to the present invention are illustrated by the following examples.

EXAMPLE 1

0.1 g. of mecobalamin, 0.1 g. of New Coccine and 98 g. of mannitol were mixed, and the mixture was then kneaded with 20 ml. of a 10% ethanolic solution of hydroxypropyl cellulose. This was granulated by means of a cylinder using a screen of the mesh 0.5 mm. and dried for 10 hrs. by blowing air maintained at about 60° C. The dried granular product was then dressed to give a product in the grain range of 1410–500μ.

The so obtained granule was of the mecobalamin content of 0.1%. The New Coccine content therein was 0.1%.

EXAMPLE 2

1 g. of mecobalamin, 7 g. of corn starch and 90 g. of mannitol were mixed, and 40 ml. of a 5% aqueous solution of hydroxypropyl cellulose was sprayed over the mixture. The resulting mixture was granulated and dried by the fluidized bed method. The dried granular product was then dressed to give a product in the grain range of about 500–105μ. This granule was referred to as Granule A.

Independently, 0.11 g. of New Coccine, 7 g. of corn starch and 91 g. of mannitol were mixed, and 40 ml. of an 5% aqueous solution of hydroxypropyl cellulose was sprayed over the mixture. The resulting mixture was then granulated and dried by the fluidized bed. The dried granular product was subsequently dressed to give a product in the grain range of about 500–105μ. This granule was referred to as Granule B.

Granule A and Granule B were mixed in the ratio of 1:9. The so obtained granule mixture was of the mecobalamin content of 0.1%. The New Coccine content was 0.1%.

EXAMPLE 3

1 g. of cobamamide, 7 g. of corn starch and 90 g. of mannitol were mixed, and the mixture was then kneaded with 20 ml. of a 10% ethanolic solution of hydroxypropyl cellulose. This was granulated by means of a cylinder using a screen of mesh 0.5 mm. and dried for 10 hrs. by blowing air maintained at about 60° C. The dried granular product was then dressed to give a product in the grain range of 1410–500μ. This granule was referred to as Granule A.

Independently, 0.22 g. of New Coccine, 7 g. of corn starch and 91 g. of mannitol were mixed, and the mixture was then kneaded with 20 ml. of a 10% ethanol solution of hydroxypropyl cellulose. This was granulated by means of a cylinder using a screen of the mesh 0.5 mm. and dried for 10 hrs. by blowing air maintained at about 60° C. The dried granular product was then dressed to give a product in the grain range of 1410–500μ. This granule was referred to as Granule B.

Granule A and Granule B were mixed in the ratio of 1:9. The so obtained granule was of the cobamamide content of 0.1%. The New Coccine content was 0.2%.

EXAMPLE 4

0.2 g. of New Coccine, 100 g. of crystalline cellulose and 100 g. of lactose were mixed and kneaded to form a wet lump with red color, and the resulting lump was dried in the fluidized-bed drier. The dried granular product was subsequently dressed by means of a sieve of the mesh 841μ. The resulting red-colored powder (100 g.) was mixed with 0.25 g. of mecobalamin, and the mixture was incorporated into No. 4 capsules with red-colored caps and white-colored bodies in the amount of 100.25 mg. per capsule.

The so obtained capsule contains 0.25 mg. of mecobalamin and 0.1 mg. of New Coccine per each capsule.

EXAMPLE 5

0.1 g. of cobamamide, 0.1 g. of New Coccine and 98 g. of mannitol were mixed, and the mixture was then kneaded with 20 ml. of a 10% ethanolic solution of hydroxypropyl cellulose. This was granulated by means of a cylinder using a screen of the mesh 0.5 mm. and dried for 10 hrs. by blowing air maintained at about 60° C. The dried granular product was then dressed to give a poduct in the grain range of 1410–500μ.

The so obtained granule was of the cobamamide content of 0.1%. The New Coccine content was 0.1%.

The embodiments of the invention in which an exclusive property or privilege is claimed are defined as follows:

1. A process for producing a solid, pharmaceutical composition comprising the steps of mixing cobamamide or mecobalamin and a pharmaceutically acceptable solid carrier to form a first mixture and then granulating said first mixture to obtain first granules thereof; separately mixing a red dye selected from the group consisting of Amaranth, Erythrocin, New Coccine, Phloxine, Rose Bengal and Acid Red, and a pharmaceutically acceptable, solid carrier, to form a second mixture and then granulating said second mixture to obtain second granules thereof; and mixing a multiplicity of said first granules with a multiplicity of second granules to form a granular mixture.

2. A process as claimed in claim 1, in which said red dye is New Coccine.

3. A process as claimed in claim 1 in which said red dye is Amaranth.

4. A process as claimed in claim 1, wherein said composition contains from 0.1 to 5 parts by weight of said red dye, per one part by weight of said cobamamide or mecobalamin.

5. A process as claimed in claim 1, including the step of forming said granular mixture into a solid capsule or tablet.

6. A solid, pharamceutical composition for oral administration, comprising: a mixture of a multiplicity of first granules with a multiplicity of second granules; said first granules consisting essentially of a pharmaceutically acceptable amount of a coenzyme $B_{12}$ substance selected from the group consisting of cobamamide and mecobalamin admixed with an orally administratable, solid, pharmaceutical carrier; said second granules consisting essentially of a pharmaceutically acceptable red dye selected from the group consisting of Amaranth, Erythrocin, New Coccine, Phloxine, Rose Bengal and Acid Red admixed with an orally administratable, solid, pharmaceutical carrier said composition having been prepared according to the process of claim 1.

7. A composition as claimed in claim 6, in which said red dye is Amaranth.

8. A composition as claimed in claim 6, in which said red dye is New Coccine.

9. A composition as claimed in claim 6, claim 7 or claim 8, in the form of a capsule or tablet.

10. A composition as claimed in claim 6, wherein said red dye is present in an amount in the range of from 0.1 to 5 parts by weight, per 1 part by weight of said cobamamide or mecobalamin.

* * * * *